US00PP13751P29

(12) United States Plant Patent
Zwetzig et al.

(10) Patent No.: US PP13,751 P2
(45) Date of Patent: Apr. 29, 2003

(54) HIBISCUS PLANT NAMED: 'PINK COMET'

(76) Inventors: Gretchen Angela Zwetzig, 8101 S. 14th St., Lincoln, NE (US) 68512; David Whitman Fleming, deceased, late of Lincoln, NE (US), by Gretchen Zwetzig, legal representative ( * ) Notice: Subject to any disclaimer, the term of this patent is extended or adjusted under 35 U.S.C. 154(b) by 0 days.

(21) Appl. No.: 10/207,254

(22) Filed: Jul. 30, 2002

(51) Int. Cl.[7] ..... A01H 5/00
(52) U.S. Cl. ..... Plt./257
(58) Field of Search ..... Plt./257

*Primary Examiner*—Bruce R. Campell
*Assistant Examiner*—W C Haas

(57) ABSTRACT

A new and distinct cultivar of winter hardy hibiscus plant named 'Pink Comet' is the result of a unique hybridization. This new and distinct cultivar is characterized primarily as to novelty by its tropical aspects, its extreme cold hardiness to Zone 4, its medium-sized, thick-textured, pink flowers with pale pink to white reverse having multiple markings of red and pink on both sides of the petals and its shiny green leaves and unusual compactness of about 2 feet, its vigorous and uniform growth habit, and its floriferous nature from midsummer until frost, and its genetic achievement as a cross between a tropical and hardy Hibiscus.

2 Drawing Sheets

BOTANICAL CLASSIFICATION

*Hibiscus moscheutos×H. rosa-sinensis.*

BACKGROUND OF THE NEW PLANT

The new plant of this invention is the result of a unique hybridization, with the breeding achievement being evidenced in the outstanding combination of characteristics exhibited by this new and distinct Hibiscus plant, which include:

(a) Refined and noticeably shiny, "Maple-like", green leaves which have relatively smooth margins and white buds with red and pink markings which combined compliments the landscape;

(b) Medium-sized flowers that are outstanding for their pink petals with pale pink to white reverse having red and pink markings on both sides of the petals;

(c) The plant being very floriferous with flowers that stay open at least one full day;

(d) The plant being small but vigorous with stouter stems compact and uniform breaking action which gives it unique landscape utility; and (e) The plant being so hardy that it can consistently withstand winter temperatures of at least −30 degrees Fahrenheit.

(f) The plant being a gentic achievement as a hybrid between a tropical and hardy Hibiscus.

SUMMARY OF THE INVENTION

'Pink Comet' was the result of a 40-year breeding program. Its ancestry includes *Hibiscus moscheutos* and *Hibiscus rosa-sinensis*. More specifically, the plant resulted from multiple crossings with an unnamed Fleming *Hibiscus rosa-sinensis* (nonpatented) and a unnamed Fleming *Hibiscus moscheutos* (nonpatented). The seedling which most nearly met all of the above named standards was selected.

This new plant first bloomed in the summer of 1989 and was selected by David Fleming and Gretchen Zwetzig on David Fleming's property in Lincoln, Nebr. Asexual propagation of the plant by cuttings and root division has shown that the unique and distinguishing features of the plant are faithfully transmitted from generation to generation and appear to be fixed.

Since its origin, the plant has bloomed from midsummer until frost, while exhibiting the aforementioned distinctive characteristics. This TROPICAL-HARDY™ Hibiscus plant greatly contributes to the market with its tropical aspect, sheer beauty and utter refinement, its compact growth habit, its enhanced resistance to disease and insects, its stability through extremes in rain and drought, and its extreme hardiness.

BRIEF DESCRIPTION OF THE DRAWINGS

The flower and foliage of the cultivar are shown in the attached photographs

More specifically, the first photograph is a close-up of the flower and the leaf. The second photograph is the reverse of the petals, close-up.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with the *Dictionary of Color* (Maerz and Paul), while general color recitations are consistent with ordinary American color terminology.

'Pink Comet' has not been observed under all possible environment conditions. It is to be understood that the phenotype may vary significantly with variations in environment such as temperature, light intensity, and day length, without, however any difference in genotype of the plant. The following botanical characteristics and observations are gathered from the plant when grown in Lincoln, Nebr. (USDA Zone 4).

THE PLANT

Parentage:

*Seed parent.—Hibiscus moscheutos*, Unnamed and unpatented Fleming seedling.

*Pollen parent.—Hibiscus rosa-sinensis* Unnamed and unpatented Fleming seedling.

Origin: A selected seedling from stated cross.

Type of plant: Hardy, herbaceous perennial with some tropical genetics.

Classification: Variety of TROPICAL-HARDY™ Hibiscus plant.

Propagation: Relatively easy to propagate; holds its distinguishing characteristics through successive cuttings and division.

Size: About 2½ feet tall and about 2 ft. wide.

Form: Symmetrical annual growth from perennial roots.

Habit: Upright and uniformly branched.

Growth: Vigorous; small and very compact. Full grown (2 ft.) in 2 years.

Hardiness: Hardy to at least −30 degrees Fahrenheit.

General health: Plant is very disease resistant against rot, aphids, spider mites, scale, white fly, etc.; sturdy through excessive drought, rain, or wind.

Propagation: Relatively easy and fast rooting in approximately 2 weeks.

Foliage:

1. *Arrangement.*—Alternate.
2. *Shape.*—Juvenile: Variable, ovate to 3-lobed leaf. Rounded base shape. Mature: Refined, "maple-like", 3–5 lobed leaf with entire to mildly serrate margins and acute apices; rounded base.
3. *Size.*—Mature leaf (petiole base to apex): Length is about 3¾ inches or 9½ cm, width is about 2¼ inches or 6 cm.
4. *Color.*—Young leaves (upper side): L-1, p.67, PLATE 22. Mature leaves: (upper side) — 6-L, p.69, PLATE 23. Veins: Slightly lighter than 3-L, p. 69, PLATE 23. Coloration of the lower leaf surface: 3-L, p. 69, PLATE 23.
5. *Surface texture.*—High sheen.
6. *Petiole length.*—About 1¼ inches or 3½ cm.
7. *Petiole color.*—Green to K-1, PLATE 46, page 115.

Stems: The stems are stout at the base, becoming more slender toward the apices; coloration is consistent with the petiole.

THE FLOWER

Blooming period: Profuse from July until frost.

Flower diameter: Medium to large; about 7½ inches (17 cm).

Borne: Singly in leaf axils, from midpoint of stems upward.

Bloom duration: Individual bloom lasts at least one full day, sometimes 2.

Form: Campanulate; petals are also very overlapping.

Bud:

1. *Length.*—About 2¼ inches (or 6 cm) on day before opening.
2. *Color.*—1-D, PLATE 3, page 29.
3. *Surface texture.*—Semi-glabrous.
4. *Duration.*—One to two weeks.

Corolla: Having 5 petals.

1. *Petal character and dimensions.*—Campanulate and very overlapping. Length is about 3¾ inches or 9.5 cm. Width is about 4½ inches or 11 cm.
2. *Coloration.*—The front of the petals are light pink with reddish pink, dash-like markings over most of the surface. The backside of the petals are pale pink to white with red markings . (a) Pale pink petals: A-4, pg. 25, PLATE 1 Coloration of lower petal surface: 2-A, pg. 27, PLATE 2. (b) Veination in petals: 6-K, pg. 25, PLATE 1. (c)Eye Zone: 6-K, pg. 25, PLATE 1. (d) Dash-like markings on both sides of the petals: 4-L, pg. 133, PLATE 55.
3. *Texture.*—Smooth.
4. *Substance.*—Thick.
5. *Shape.*—Campanulate and very overlapping.

Reproductive organs:

1. *Staminal column.*—Stamen along basal two-thirds. Stamen length: About 2¼ inches ( or5.5 cm). Stamen color: 2-K, PLATE 9, page 41. Pollen color: 1-B, PLATE 9, page 41.
2. *Style.*—Terminates upper one-third of staminal coumn. Stigmatic lobe color: J-3, PLATE 1, page 25.

Calyx: Connate at the base; about 1½ inches (or 4.5 cm) in length. Color: Medium green.

Stipules: None.

Epicalyx: Whorl of bracts.

1. *Shape.*—10 to 12 slender, sword-shaped bractlets.
2. *Length.*—About 1 inch (or 2¼ cm).
3. *Color.*—5-K, PLATE 22, page 67.

Penduncle:

1. *Length.*—About 2½ inches (or 6.5 cm).
2. *Strength.*—Stiff and sturdy.
3. *Color.*—Light to medium green.

GENERAL OBSERVATIONS

This plant, as a hybridized TROPICAL-HARDY™ Hibiscus, is valuable to the landscape market for its improvements in tropical aspect, thicker-textured and uniquely marked flowers and buds, shiny and refined, "Maple-like" green foliage on a much more compact plant, its all-around vigor, good breaking action, and adaptation to extreme environments, including the ability to consistently survive winter temperatures of at least −30 degrees Fahrenheit.

It is claimed:

1. A new and distinct cultivar of Hibiscus plant, as herein shown and described.

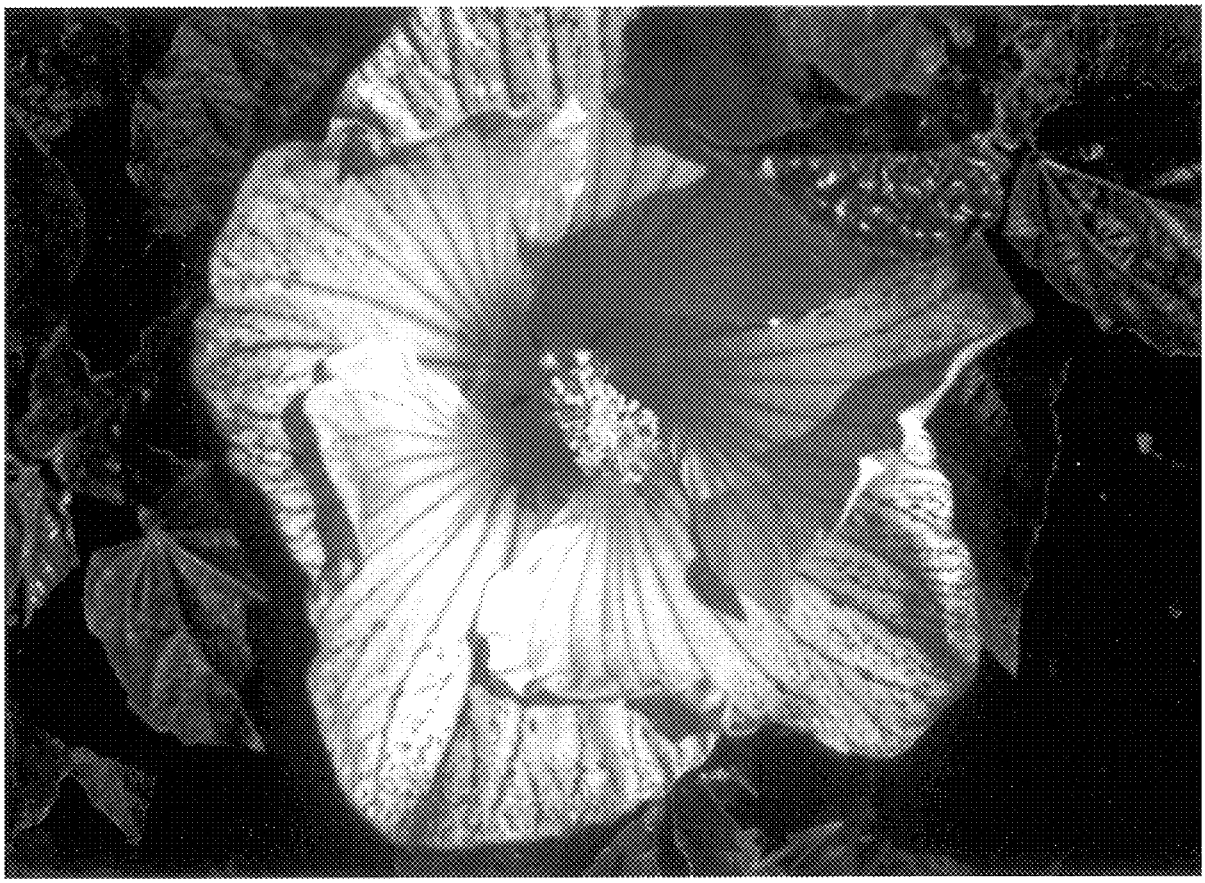

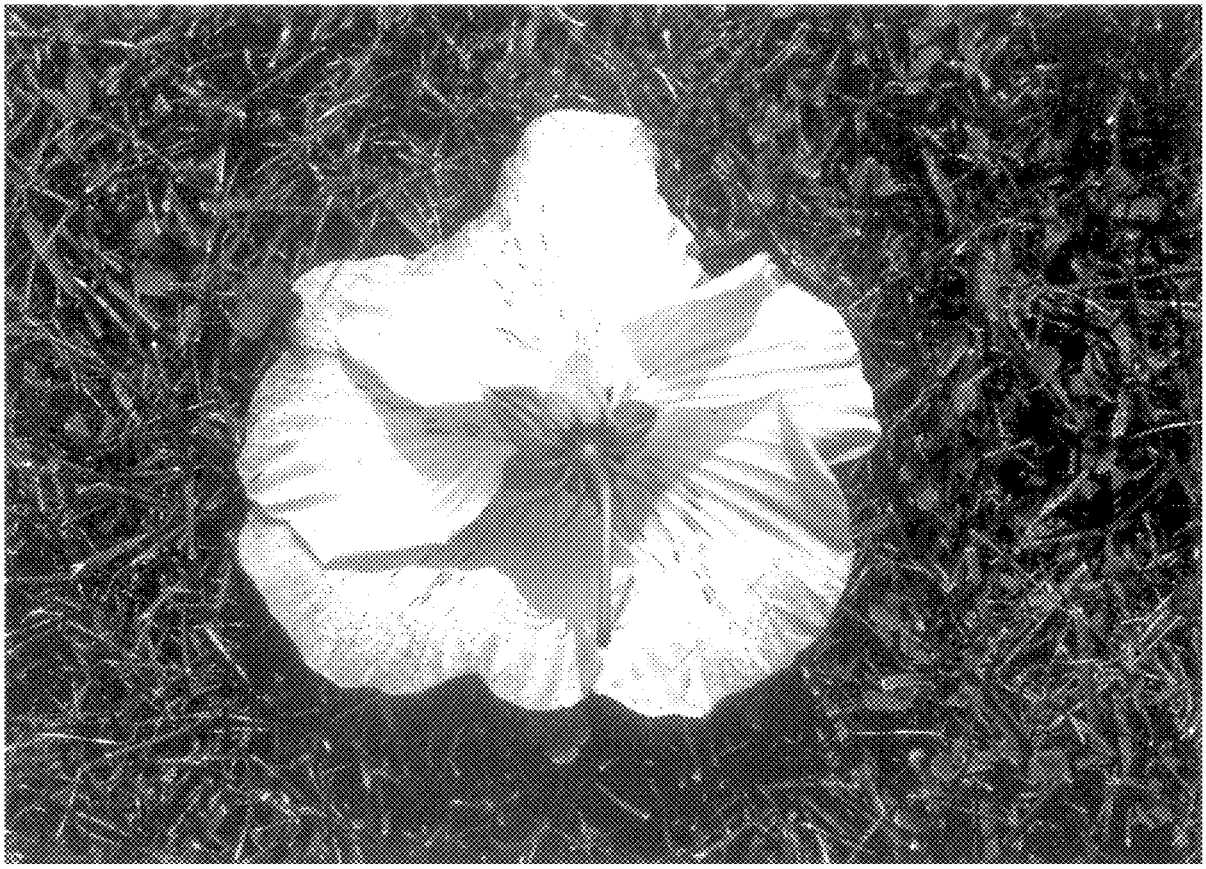

* * * * *